United States Patent [19]
Mager

[11] Patent Number: 5,899,078
[45] Date of Patent: May 4, 1999

[54] METHOD AND APPARATUS FOR REDUCING ENERGY USE BY REFRIGERATION DOOR AND FRAME HEATERS

[75] Inventor: A. Malcolm Mager, Hopedale, Mass.

[73] Assignee: Peak Energy Systems, Inc., Hopedale, Mass.

[21] Appl. No.: 08/823,480

[22] Filed: Mar. 25, 1997

[51] Int. Cl.[6] ............................. F25D 21/00; B60S 1/54
[52] U.S. Cl. ............................. 62/80; 62/150; 62/275
[58] Field of Search .................... 62/275, 248, 176.2, 62/150, 140, 80; 454/121, 75; 165/231; 219/203

[56] References Cited

U.S. PATENT DOCUMENTS

| | | | |
|---|---|---|---|
| 3,495,416 | 2/1970 | Morrissey, Jr. et al. | 62/275 X |
| 3,902,040 | 8/1975 | Ikeda et al. | 219/203 |
| 3,939,666 | 2/1976 | Bashark | 219/203 X |
| 4,260,876 | 4/1981 | Hochheiser | 219/203 X |
| 4,261,179 | 4/1981 | Dageford | 62/275 X |

*Primary Examiner*—William Wayner
*Attorney, Agent, or Firm*—Lee & Hollander

[57] ABSTRACT

A system is provided for reducing power consumption of door and frame heaters of refrigerating devices while maintaining protection against condensation. One or more condensation sensors are attached to the door and are monitored by control circuitry which controls power applied to the door or frame heater. Condensation on the sensor will increase the conductivity of the sensor, which is detected by the control circuitry. When condensation occurs, power is applied to the heater until the condensation is eliminated. The invention includes two different condensation sensor configurations.

14 Claims, 2 Drawing Sheets

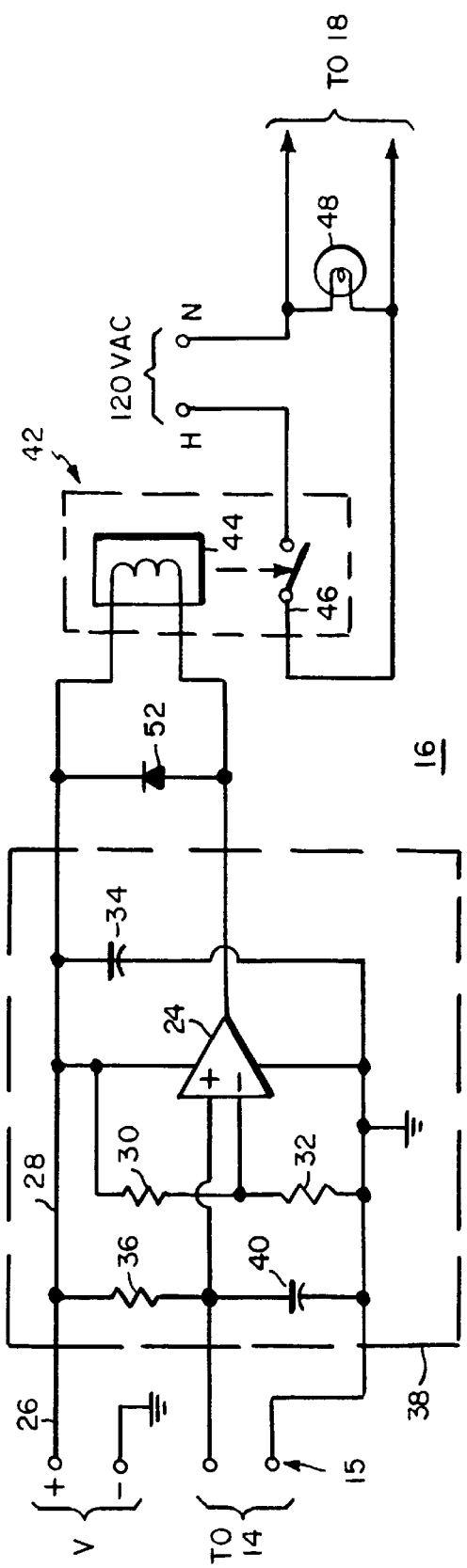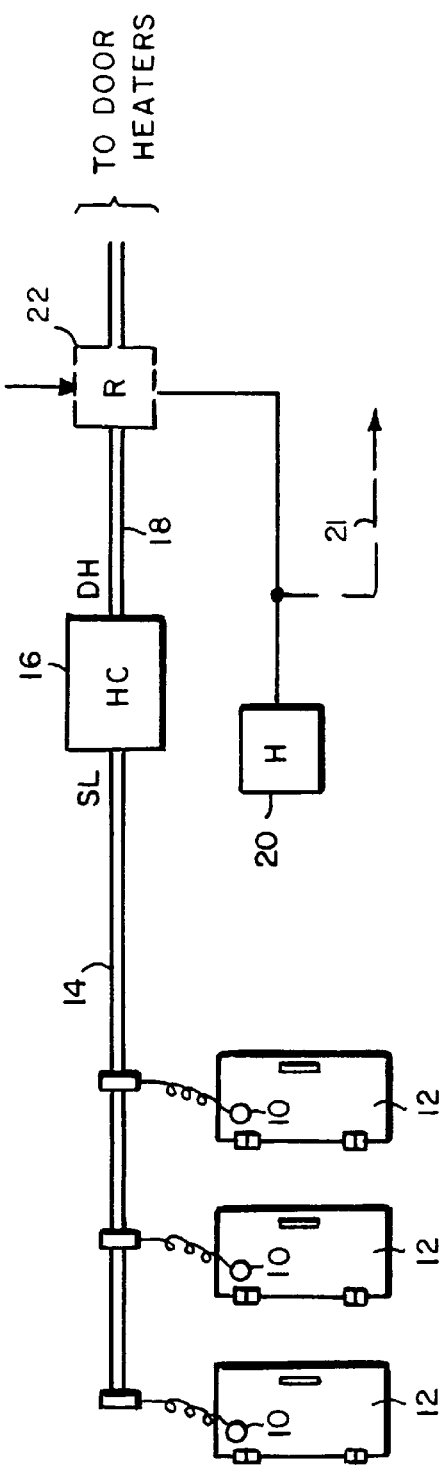
FIG. 2
FIG. 1

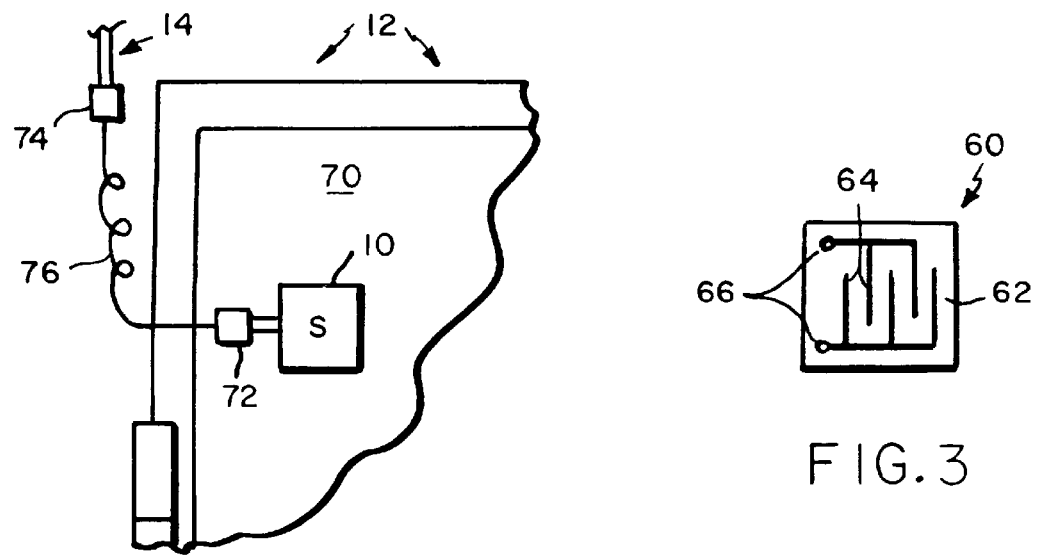
FIG. 4
FIG. 3
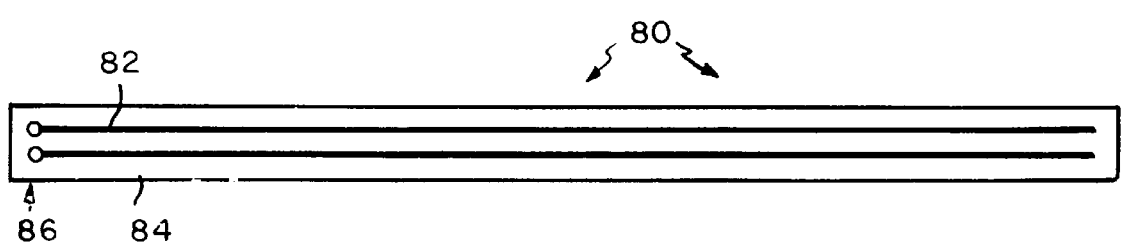
FIG. 5

METHOD AND APPARATUS FOR REDUCING ENERGY USE BY REFRIGERATION DOOR AND FRAME HEATERS

FIELD OF THE INVENTION

This invention is related to energy conserving devices, and more particularly to devices for reducing the electricity usage of frame and door heaters used in refrigeration equipment.

BACKGROUND OF THE INVENTION

Retail and other establishments that store and sell refrigerated items frequently must be concerned with condensation problems. It is a common practice in commercial refrigerators and freezers, referred to below as coolers, to utilize a glass display door with a large window in it to provide easy access for a customer while allowing the customer to easily see what is inside the cooler. Frequently, the window makes up the majority of the door panel. Under adverse environmental conditions, condensation on the door frames and door window panes can be a problem.

For example, a door to a cooler in a store may be opened frequently by customers. When this happens, the inside of the door, which may be at a temperature of 2° C. to 5° C. (35° F. to 40° F.), is immediately exposed to the ambient air in the store. Depending on the temperature and humidity levels of the ambient air, condensation may form on the cold inside surfaces of the door. If the humidity is relatively high, heavy condensation may form almost immediately, which can completely obscure the view through the door glass. This obviously is detrimental to the purpose of the window, which is to provide a clear view inside the cooler. Additionally, the condensation may be heavy enough to cause the door to drip when opened. This is a particular problem in retail stores where it can create a hazardous puddle or get a customer wet and thus dampen their enthusiasm for that store.

In an effort to reduce or eliminate these problems, it has become a common practice to employ heaters in door windows and door frames of refrigeration equipment. These devices, which will be referred to as door heaters below, use small electrical heating elements to raise the temperature of the door glass or frame sufficiently that condensation is reduced or eliminated. Door heaters are used in both refrigerators and freezers, and both type of units will be understood to be included in the term cooler as it is used below. There is a significant energy cost associated with using such devices, however. It takes energy to power the door heaters, and the heat generated by these heaters must be removed from the refrigerated volume by the refrigeration system. The costs involved with door heaters can be substantial.

SUMMARY OF THE INVENTION

The goal of the present invention is to reduce the costs associated with the use of door heaters without impairing their ability to eliminate condensation. In order to do this, the present invention takes advantage of the fact that heating a door window or frame is not always necessary. Whether or not condensation forms on a door depends on several factors, including the temperature and humidity both inside and outside of the refrigerator, the length of time that the door is opened, how often the door is opened, and other factors.

Frequently, conditions are such that condensation is not likely to form, and in such case, the door heater is not needed. For example, a cooler used in a retail establishment may be heavily used and frequently opened at certain times of peak sales while being used infrequently at other times. Additionally, ambient humidity may often be low enough that condensation is very unlikely to form. Since many unpredictable factors influence the likelihood of condensation forming, timers, humidity measurement devices, and the like will not provide optimum reduction of energy usage while achieving the goal of eliminating condensation.

The present invention reduces the door heater energy consumption while still preventing condensation by using a sensor to detect when condensation is just starting to form. Power is applied to the door heaters only when required and only for so long as required to eliminate the condensation. The present invention is adapted to being retrofitted onto existing coolers, or may be built in as an integral part of the cooler.

The invention includes one or more condensation sensors which are attached to the surface of the door or frame to be protected. The sensor is subject to the same conditions as the door, and condensation will start to form on the sensor at the same time as on the door. The sensor is connected to circuitry which detects when condensation starts to form and, in response, applies power to the door heater. The system continuously monitors the sensor so that when conditions change such that condensation is no longer present, power may be removed from the door heaters. Different sensor configurations are disclosed which have advantages in different applications.

DESCRIPTION OF THE DRAWINGS

The advantages and operation of the present invention are more fully described in the following description of the preferred embodiment and by reference to the drawings, of which:

FIG. 1 is a diagram of a typical installation using the invention;

FIG. 2 is a schematic diagram of the control circuitry of the invention;

FIG. 3 shows a printed-circuit board type of condensation sensor;

FIG. 4 shows details of how a condensation sensor may be attached to a cooler door; and FIG. 5 shows a strip condensation sensor.

DESCRIPTION OF THE PREFERRED EMBODIMENT

Referring to FIGS. 1 and 2, the construction and general operation of the invention will be described. FIG. 1 is a block diagram showing the major components of the invention. In FIG. 1, one or more condensation sensors 10 are attached to doors 12 of a cooler. The sensors are each connected to two sensor lines 14 which run to the door heater control circuitry 16, discussed in detail below. The heater control circuitry 16 monitors the sensors 10 and detects when condensation begins to form. In response to this detection, the control circuit 16 applies power for the door heaters to lines 18 which go to the cooler door heaters. Only one sensor 10 is needed when there is only one door. However, many commercial coolers have a plurality of doors, and, as described below, the invention may advantageously use a separate sensor on each door of a single cooler with these sensors connected to a single control circuit. Normally, separate control circuits are used with each individual cooler unit, since the conditions in each unit may not be the same and because each unit will have its own separate door heater system.

Optionally, a humidity sensor 20, such as humidistat or similar device, may be used to provide override control of the door heaters by providing a signal when the ambient humidity exceeds a selected level. If installed, the humidity sensor 20 controls a relay 22 which disconnects the door heaters from the control circuit 16 and connects the heaters directly to a power source, typically 120 VAC. Humidity sensor 20 is located outside the cooler and applies power to the door heaters when unusually high levels of humidity outside the cooler would cause condensation on the outside of the doors without door heater power applied, typically around 70 to 80%. If multiple control circuits are used with a plurality of heater control circuits 16, the output from a single humidistat can be used for all of the systems by providing in each door heater power line a relay 22 which is controlled by the humidistat output, as illustrated by dashed line 21.

FIG. 2 is a schematic diagram showing details of the control circuitry 16. Each of the condensation sensors 10 is connected across terminals 15 connected to the sensor lines 14. The conductivity of the sensors 10 changes in response to the onset of condensation formation, as described in more detail below. When multiple sensors are used, they may be connected in parallel across the sensor lines 14.

One of the sensor lines 14 is connected to ground; the other is applied to the non-inverting input of an op-amp 24. In the described embodiment, op-amp 24 is an LM311 type. A low, DC voltage, typically 12 volts, is applied between a V+ voltage bus 26 and ground. A 4.7 $\mu$F capacitor 34 is connected between +V and ground and provides by-pass filtering of the supply voltage. The V+ voltage is applied to op-amp 24 via lines 28 to provide power to the op-amp. The V+ voltage is also applied to the inverting input of the op-amp via a voltage divider made up of resistors 30 and 32 connected between V+ and ground. In the described embodiment, resistors 30 and 32 are each 4.7 k$\Omega$, and the non-inverting input is held at a voltage of 6 volts.

A resistor 36 is connected between V+ and the sensor line applied to the op-amp non-inverting input. In the described embodiment, resistor 36 is 10 M$\Omega$. A capacitor 40 of 0.1 $\mu$F is connected between the sensor line and ground. The condensation sensors 10 are typically connected to control circuit 16 via unshielded wires of many feet in length. Capacitor 40 ensures that the control circuitry is not triggered by spurious signals picked up on the sensor lines 14.

The described circuitry in dashed box 38 serves as a threshold detector which provides an output when the conductivity across sensor lines 14 exceeds a set value. As described below, the condensation sensors 20 comprise two conducting patterns with lines closely spaced together on an insulating substrate. Normally, when no condensation is present on the surface of the condensation sensors, the resistance between lines 14 is very high, on the order of 20 to 100 megohms; and the non-inverting input to the op-amp will be held well above 6 volts by resistor 36. When condensation begins to form on the surface of the sensor, the conductivity increases rapidly, and when the resistance across lines 14 drops below about 10 M$\Omega$, the output of op-amp 24 will switch from high to low.

The output of op-amp 24 is applied to one terminal of the coil 44 of a relay 42 which controls power to the cooler door heaters. The second terminal of coil 44 is connected to the V+ bus 28. Coil 44 controls relay terminals 46, which are normally open. In the described embodiment, terminals 46 are connected in series between the door heaters and the power source for the door heaters, normally 120 VAC; however, other configurations may be used. An indicator light 48 may be connected across door heater lines 18 to indicate when the door heaters are operating.

In the absence of condensation, the output of the op-amp is high, and relay 44 is inactivated. When condensation is detected by one or more of the condensation sensors 14, the output of op-amp 24 goes low, applying power to coil 44 and energizing relay 44. This turns on the door heaters. After the condensation has been eliminated by the door heaters, the output of the op-amp will return high, and power is removed from the door heaters. Diode 52 is connected across the relay coil 42 to shunt any self-inductive currents which may be produced by the relay coil when power to it is turned off.

FIG. 3 shows a first embodiment 60 of a condensation sensor that may be used with the present invention. Sensor 60 comprises a PCB board with two interlaced conductor patterns 64 on the PCB substrate 62. In the described embodiment, the sensor is about one inch on each side. The interlaced pattern consists of parallel conductors about 0.05 inches wide and separated by about 0.10 inches. Two terminal pads 66 are provided for soldering wires to connect the sensor to the rest of the system. It is preferable that the PCB conductors be coated with solder or otherwise protected from possible corrosion from the condensation.

FIG. 4 shows the preferred method for mounting a condensation sensor, such as that shown in FIG. 3. The sensor 10 is adhesively mounted to the surface to be protected, in this case, the glass panel 70 of a cooler door 12. The sensor is connected to a first jack 74 via wires between the jack and terminal pads 66. If desired, the jack may be mounted directly on the substrate of the PCB sensor 10. A second jack 74 connected to the sensor lines 14 is mounted to the inside of the cooler. A flexible cable connects jacks 74 and 72 to connect the sensor 60 with control circuit 16. RJ-11 telephone jacks are suitable for jacks 72 and 74, and a spiral telephone-type cable may be used for cable 76. This provides for a durable, flexible connection between the sensors and the sensor lines as the door is opened and closed, while allowing the sensor to be easily disconnected to ease door cleaning or to allow the door to be removed.

In FIG. 5, a condensation sensor 80 is shown which has advantages over the sensor of FIG. 3. In the sensor of FIG. 5, two long, parallel conductive strips 82 are formed on a clear, flexible, substrate 84. The substrate may be made of a clear adhesive-backed material such as Mylar, vinyl, or polycarbonate. The conductors 82 are preferably formed by screening a conductor made of one part silver and one part bonding agent onto the substrate 84. Alternatively, the conductors 82 may be formed of conductive carbon ink or wire conductors. Two terminals 86 are provided at the end of the strip for connecting the sensor. In the described embodiment, the conductors 82 are 0.10 inches wide by 8 inches long, and are separated by about 0.05 inches.

Due to the nature of the flexible substrate, conductors 82 cannot be protected after deposition by a layer of solder. Over long periods of time, nickel or tin based alloys may eventually suffer from electrophoretic migration of small amounts of the metal between the conductors caused by the voltage between the conductors. Due to the high resistance levels being measured as condensation forms, even minimal amounts of migration may increase the conductivity sufficiently to affect the performance of the sensor. Thus, carbon ink or an equivalent material which minimizes such migration is a preferred material for the conductors 82.

The sensor of FIG. 5 has advantages over other types of sensors in some applications. Since condensation may begin to form at one location on a door before forming elsewhere, and since condensation in the central portion of the door glass is most important for visibility, a condensation sensor that may be centrally mounted is sometimes preferable. Since it is mostly clear, the sensor of FIG. 5 may be mounted more towards the center of the door glass, where visibility is most important, without being unattractive. It extends over a larger area and is thus more likely to sense condensation forming under conditions where condensation is just beginning to form in isolated spots.

There has been described a new and useful method and apparatus for reducing the energy required to avoid condensation on cooler doors. While the operation and advantages of the invention have been described with reference to the exemplary embodiments described above, it should be appreciated that modifications to these embodiments will be made by those of ordinary skill in the art in applying the invention to different situations and applications. Accordingly, the present invention should not be limited by the embodiments described above, but rather the scope of the invention should be interpreted only in accordance with the following claims.

What is claimed is:

1. A method of controlling the application of power to a condensation-preventing heater in a refrigeration unit, comprising the steps of:

providing two electrically isolated, conductive patterns in close proximity to one another, said patterns being located on the refrigeration unit close to said heater;

measuring the resistance between the conductive patterns;

comparing said measured resistance with a threshold value;

measuring the humidity level outside of said refrigeration unit;

comparing said measured humidity level to a predetermined humidity level; and applying power to said heater either when the measured resistance is less than said threshold value or when the measured humidity exceeds said predetermined level.

2. Apparatus for controlling a condensation-preventing heater in a refrigeration unit, comprising:

a plurality of sensing means connected in parallel, for detecting the presence of condensation, each of said sensing means being mounted on the refrigeration unit in proximity to said heater;

means, responsive to a control signal, for controlling power to said heater; and control means, responsive to the detection of condensation by said sensing means, for providing said control signal so that power is applied to said heater only when condensation is present;

wherein each of said sensing means further comprises:
    an insulating substrate;
    two electrically-isolated conductors arranged so that one conductor lies in close proximity to the other conductor;
    whereby condensation forming on said sensing means raises the conductivity between said conductors; and
    wherein said control means includes means responsive to said increase in conductivity for providing said control signal, including means for measuring the resistance between said conductors and for providing said control signal when said resistance is below a predetermined threshold resistance.

3. The apparatus of claim 2 wherein:

said insulating substrate includes a printed circuit board; and said two conductors includes two sets of interlaced conductive elements formed on the surface of said printed circuit board conductors.

4. The apparatus of claim 3 wherein said conductors are 0.05 inches in width and wherein the elements of one set are separated from the elements of the other set by 0.1 inches.

5. The apparatus of claim 2 wherein:

said insulating substrate includes an insulating material in the form or a long, flat strip; and said two conductors include two, electrically isolated conductive lines running substantially parallel to each other along the length of said substrate.

6. The apparatus of claim 5 wherein the conductive lines are formed by depositing a conductive ink on one surface of said clear insulating material.

7. The apparatus of claim 6 wherein the clear, insulating material is formed of vinyl.

8. The apparatus of claim 6 wherein the clear, insulating material is formed of polycarbonate.

9. The apparatus of claim 6 wherein the clear, insulating material is formed of transparent vinyl.

10. The apparatus of claim 6 wherein the clear, insulating material is formed of transparent polycarbonate.

11. The apparatus of claim 2 wherein said two conductive lines are each 0.1 inches wide and are separated by 0.05 inches.

12. The apparatus of claim 2 wherein said control means includes means for measuring the resistance between said conductors and for providing said control signal when said resistance is below a predetermined threshold resistance.

13. The apparatus of claim 12 wherein the threshold resistance is 10 megohms.

14. The apparatus of claim 2 further comprising:

means for measuring the humidity level outside of said refrigeration unit;

means for comparing said measured humidity to a predetermined humidity level; and means for applying power to said heater, independent of the control signal, when the measured humidity exceeds said predetermined level.

* * * * *